United States Patent [19]

Kyburz

[11] 4,089,861
[45] May 16, 1978

[54] (+)-(S)-ENANTIOMER OF 3-{2-[4-(8-FLUORO-10,11-DIHYDRO-2-METHYL-DIBENZO[b,f]THIEPIN-10-YL)-1-PIPERAZINYL]-ETHYL}-2-OXAZOLIDINONE

[75] Inventor: Emilio Kyburz, Reinach, Switzerland

[73] Assignee: Hoffmann-La Roche, Inc., Nutley, N.J.

[21] Appl. No.: 690,325

[22] Filed: May 26, 1976

[30] Foreign Application Priority Data

Jun. 6, 1975  Switzerland ............ 7353/75
Mar. 19, 1976  Switzerland ............ 3506/76

[51] Int. Cl.² ............................................. C07D 413/14
[52] U.S. Cl. ................................. 544/369; 424/250

[58] Field of Search .................................. 260/268 TR

[56] References Cited

U.S. PATENT DOCUMENTS

| 3,954,764 | 5/1976 | Gerecke et al. | 260/268 TR |
| 3,954,769 | 5/1976 | Gerecke et al. | 260/268 TR |
| 3,966,737 | 6/1976 | Gerecke et al. | 260/268 TR |

*Primary Examiner*—Nicholas S. Rizzo
*Attorney, Agent, or Firm*—Samuel L. Welt; George M. Gould; William G. Isgro

[57] ABSTRACT (+)-(S)-enantiomer of 3-{2-[4-(8-fluoro-10,11-dihydro-2-methyldibenzo[b,f]thiepin-10-yl)-1-piperazinyl]-ethyl} -2-oxazolidinone, active as a neuroleptic agent, is described.

2 Claims, No Drawings

(+)-(S)-ENANTIOMER OF 3-{2-[4-(8-FLUORO-10,11-DIHYDRO-2-METHYL-DIBENZO[b,f]THIEPIN-10-YL)-1-PIPERAZINYL]-ETHYL}-2-OXAZOLIDINONE

BRIEF SUMMARY OF THE INVENTION

The invention relates to an optically active dibenzo[b,f]thiepin derivative, namely, the (+)-(S)-enantiomer of 3-{2-[4-(8-fluoro-10,11-dihydro-2-methyldibenzo[b,f]thiepin-10-yl)-1-piperazinyl]-ethyl}-2-oxazolidinone characterized by the formula

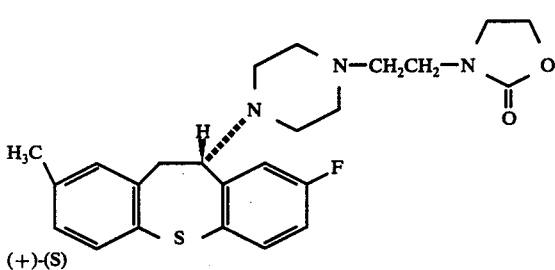

and addition salts thereof with pharmaceutically acceptable acids, which are active as neuroleptic agents.

DETAILED DESCRIPTION OF THE INVENTION

The invention relates to an optically active dibenzo[b,f]thiepin derivative, namely, the (+)-(S)-enantiomer of 3-{2-[4-(8-fluoro-10,11-dihydro-2-methyldibenzo[b,f]thiepin-10-yl)-1-piperazinyl]-ethyl}-2-oxazolidinone characterized by the formula

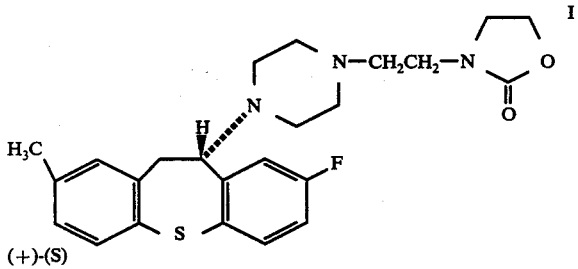

and addition salts thereof with pharmaceutically acceptable acids.

The (+)-enantiomer of formula I is a compound which, in chloroform solution and in sodium light (D-line, $\lambda$ = 589 m$\mu$), rotates the light in a positive direction. This (+)-enantiomer has the (S)-configuration.

The corresponding (−)-enantiomer is the compound which, in chloroform solution, rotates the sodium light in a negative direction. This (−)-enantiomer has the (R)-configuration.

The (+)-(S)-enantiomer and pharmaceutically acceptable salts thereof provided by the present invention possess strong central depressant and neuroleptic properties. Significantly and advantageously, this (+)-(S)-enantiomer and its pharmaceutically acceptable salts possess only slight toxicity and relatively insignificant cataleptic side effects. Accordingly, they can be utilized, for example, for the treatment of acute or chronic schizophrenia and also as tranquilizers.

The (+)-(S)-enantiomer of formula I and its salts can be prepared as follows:

(a) by resolving racemic 3-{2-[4-(8-fluoro-10,11-dihydro-2-methyl-dibenzo[b,f]thiepin-10-yl)-1-piperazinyl]-ethyl}-2-oxazolidinone into its enantiomers and isolating the (+)-(S)-enantiomer, or (b) by reacting the corresponding enantiomer of 1-(8-fluoro-10,11-dihydro-2-methyl-dibenzo[b,f]thiepin-10-yl)-piperazine with a 2-(2-X-ethyl)-oxazolidinone, wherein X is a leaving group, such as a halogen atom (preferably chlorine or bromine) or an alkyl- or aryl-substituted sulfonyloxy residue (such as methane-, benzene-, toluene- or bromobenzenesulfonyloxy), and, if desired, converting the product obtained into a salt.

The racemic 3-{2-[4-(8-fluoro-10,11-dihydro-2-methyl-dibenzo[b,f]-thiepin-10-yl)-1-piperazinyl]-ethyl}-2-oxazolidinone used as the starting material in process aspect (a) can be prepared, for example, by heating 3-[2-(1-piperazinyl)-ethyl]-2-oxazolidinone with 10-chloro-8-fluoro-10,11-dihydro-2-methyl-dibenzo[b,f]thiepin in an organic solvent, conveniently, in a chlorinated hydrocarbon such as chloroform or methylene chloride. The 3-[2-(1-piperazinyl)-ethyl]-2-oxazolidinone is obtained, for example, by condensing N-benzylpiperazine with 3-(2-chloroethyl)-2-oxazolidinone in the presence of an acid-binding agent such as potassium carbonate or triethylamine and subsequently removing the N-benzyl group by hydrogenolysis. The preparation of 10-chloro-8-fluoro-10,11-dihydro-2-methyl-dibenzo[b,f]thiepin is described further in Example 1 hereinafter.

The resolving of racemic 3-{2-[4-(8-fluoro-10,11-dihydro-2-methyldibenzo[b,f]thiepin-10-yl)-1-piperazinyl]ethyl}-2-oxazolidinone into its optical isomers is carried out by reaction with an optically active organic acid. Exemplary of such acids are tartaric acid, malic acid, mandelic acid, di-O-benzoyl tartaric acid (2,3-dibenzoyloxy-succinic acid), di-O-toluoyl-tartaric acid, camphoric acid, camphor-10-sulfonic acid (2-oxo-10-bornanesulfonic acid), 3-bromo-camphor-(8 or 10)-sulfonic acid [3-endo-bromo-2-oxo (8 or 10)-bornanesulfonic acid], diacetone-2-keto-gulonic acid (2,3:4,6-di-O-isopropylidine-$\alpha$-xylo-2-hexulofuranosonic acid) or 2,2'-(1,1'-dinaphthyl)-phosphoric acid. As the solvent there can be used a polar organic solvent, for example, a di(lower alkyl) ketone such as acetone or methyl ethyl ketone, or a lower alkanol such as methanol or ethanol. An especially preferred resolving agent is (+)-camphor-10-sulfonic acid in a di(lower alkyl) ketone, preferably, acetone. This process can be carried out over a wide range of temperatures; a temperature between about room temperature and the boiling point of the reaction mixture is generally preferred. According to a preferred embodiment of this procedure, racemic 3-{2-[4-(8-fluoro-10,11-dihydro-2-methyl-dibenzo[b,f]thiepin-10-yl)-1-piperazinyl]-ethyl}-2-oxazolidinone is heated under reflux in acetone with (+)-camphor-10-sulfonic acid and the precipitated, optically active salt is separated.

In general, it is preferred to accelerate the crystallization of the optically active salt from the solution by seeding the solution with a small amount of the same salt in solid form.

The desired (+)-(S)-enantiomeric base can be obtained from the optically active salt by neutralization according to known procedures, for example, by treatment with an aqueous alkali metal hydroxide or, preferably, by chromatography utilizing a basic material such as aluminum oxide. The base is purified according to known procedures, for example, by chromatography and/or recrystallization utilizing an organic solvent, for example, a lower alkanol such as ethanol.

In order to increase the yield of the desired (+)-(S)-enantiomer, the (−)-(R)-enantiomer obtained can be converted into the racemic form and this latter form can again be resolved into the optical antipodes. The conversion into the racemate can be carried out catalytically or non-catalytically. The catalytic racemization can be carried out, for example, in a mixture of a lower alkanecarboxylic acid such as acetic acid and a lower alkanol such as mentioned, at a temperature in the range of from about 20° C. to about 180° C., with hydrogen gas and a noble metal catalyst such as Raney nickel, Raney cobalt or palladium. According to a non-catalytic racemization procedure, the (−)-(R)-enantiomer is heated with an aqueous acid, for example, a lower sulfonic acid such as methanesulfonic acid or p-toluenesulfonic acid, or an inorganic acid such as hydrochloric acid or sulfuric acid in order to remove the side chain. The racemic 10-hydroxy compound obtained is then halogenated, for example, with thionyl chloride or bromide or with a hydrogen halide in the presence of an acid-binding agent such as hydrogen chloride and calcium chloride, and the resulting racemic 10-chloro compound is reacted with 3-[2-(1-piperazinyl)ethyl]-2-oxazolidinone as described earlier. According to another non-catalytic racemization procedure, the hydrogen atom in the 10-position of the (−)-(R)-enantiomer is replaced by a reactive metal atom, utilizing, for example, an alkali metal hydride, alkali metal amide or alkali metal lower alkanolate such as tert. butylate or ethylate, in an inert organic solvent or, where an alkali metal amide is used, in liquid ammonia at a temperature in the range of from about room temperature to about the boiling point of the solvent or at the temperature of liquid ammonia as the case may require. After reacting the resulting metal derivative with a proton donor, for example, water or an aqueous acid such as acetic acid, there is obtained racemic 3-{2-[4-(8-fluoro-10,11-dihydro-2-methyl-dibenzo[b,f]thiepin-10-yl)-1-piperazinyl]-ethyl}-2-oxazolidinone which can be resolved into the enantiomers in the manner described earlier.

The enantiomer of 1-(8-fluoro-10,11-dihydro-2-methyl-dibenzo[b,f]thiepin-10-yl)-piperazine used as the starting material in process aspect (b) has the (+)-(S)-configuration and is prepared, for example, by reacting racemic 10-chloro-8-fluoro-10,11-dihydro-2-methyl-dibenzo[b,f]thiepin with N-carbethoxy-piperazine, removing the N-carbethoxy group hydrolytically and obtaining the optical antipodes by resolving the product obtained. The resolution can be carried out in essentially the same manner as described earlier for the resolution of racemic 3-{2-[4-(8-fluoro-10,11-dihydro-2-methyl-dibenzo[b,f]thiepin-10-yl)-1-piperazinyl]-ethyl}-2-oxazolidinone. The 3-(2-X-ethyl)-2-oxazolidinone used in process aspect (b) is prepared, for example, by warming the ethanol formed by distillation and treating the 3-(2-hydroxyethyl)-2-oxazolidinone obtained with a halogenating agent, for example, thionyl chloride or bromide, or with an alkyl-substituted or aryl-substituted sulfonic acid halide, such as methanesulfonic acid, benzenesulfonic acid, toluenesulfonic acid or bromobenzenesulfonic acid chloride or bromobenzenesulfonic acid chloride or bromide.

The reaction of the (+)-(S)-enantiomer of 1-(8-fluoro-10.11-dihydro-2-methyl-dibenzo[b,f]thiepin-10-yl)-piperazine with a 3-(2-x-ethyl)-2-oxazolidinone, wherein X is a leaving group, is conveniently carried out in an inert organic solvent, for example, in an aromatic hydrocarbon such as benzene or toluene, a chlorinated hydrocarbon such as chloroform, an ether such as dioxane or dimethoxyethane, a lower alkanol such as methanol or ethanol, a ketone such as acetone or methyl ethyl ketone, dimethylformamide or dimethylsulfoxide. It is preferred to carry out the reaction in the presence of an acid-binding agent, for example, in the presence of an alkali metal carbonate or in the presence of an inert organic base such as triethylamine. The reaction is preferably carried out at a temperature in the range of from about room temperature to about the boiling point of the reaction mixture.

The (+)-(S)-3-{2-[4-(8-fluoro-10,11-dihydro-2-methyl-dibenzo[b,f]thiepin-10-yl)-1-piperazinyl]-ethyl}-2-oxazolidinone of formula I forms salts with inorganic acids, for example, with hydrohalic acids such as hydrochloric acid and hydrobromic acid and with other mineral acids such as sulfuric acid, phosphoric acid and nitric acid, and with organic acids, for example, tartaric acid, citric acid, camphor-10-sulfonic acid, methane- or ethanesulfonic acid, toluenesulfonic acid, salicylic acid, ascorbic acid, maleic acid, mandelic acid, or the like. The preferred salts are the hydrohalides, especially the hydrochlorides, the maleates and the methanesulfonates. The acid addition salts are preferably prepared in a suitable solvent, for example, ethanol, acetone or acetonitrile by treating the free base with an appropriate non-aqueous acid. Because of the two nitrogen atoms on the piperazine moiety, there can be obtained salts containing either one or two mol equivalents of acid per mol equivalent of base, that is, mono or di salts. Depending on the molar ratio between the free base and the acid used and depending on the solubility of the mono or di salts in the solvent used, there is obtained a mono or a di salt.

The (+)-(S)-3-{2-[4-(8-fluoro-10,11-dihydro-2-methyl-dibenzo[b,f]thiepin-10-yl)-1-piperazinyl]-ethyl}-2-oxazolidinone of formula I is a crystalline solid substance which has a relatively good solubility in dimethylsulfoxide, dimethylformamide and in chlorinated hydrocarbons, such as chloroform and methylene chloride. The (+)-(S)-enantiomer is somewhat less soluble in alkanols such as methanol and ethanol and is relatively insoluble in water.

The acid addition salts of (+)-(S)-3-{2-[4-(8-fluoro-10,11-dihydro-2-methyl-dibenzo[b,f]thiepin-10-yl)-1-piperazinyl]-ethyl}-2-oxazolidinone are crystalline solid substances, which have a good solubility in dimethylsulfoxide and dimethylformamide and in lower alkanols such as methanol and ethanol and are also soluble to some extent in chloroform, methylene chloride and water. The acid addition salts of the (+)-(S)-enantiomer are relatively insoluble in benzene, ether and petroleum ether.

The (+)-(S)-3-{2-[4-(8-fluoro-10,11-dihydro-2-methyl-dibenzo[b,f]thiepin-10-yl)-1-piperazinyl]-ethyl}-2-oxazolidinone has demonstrated a toxicity in the mouse (LD 50) of greater than 8000 mg/kg p.o. (after 24 hours) and 2100 mg/kg p.o. (after 10 days) and a catelepsy activity (ED 50) in the rat of 34 mg/kg i.p., which are indicative of a slight toxicity and insignificant cataleptic side effects. Further, the (+)-(S)-3-{2-[4-(8-fluoro-10,11-dihydro-2-methyl-dibenzo[b,f]thiepin-10-yl)-1-piperazinyl]-ethyl}-2-oxazolidinone possesses a strong neuroleptic activity — 316% increase of the homovanillic acid titre in the brain of the rat after administration of 10 mg/kg p.o. an 248% increase after administration of 25 mg/kg p.o. — and a strong central-depressant activity — 50% reduction of the retention time in the rotating rod test (ED 50) at 2.6 mg/kg p.o. This (+)-(S)-enantiomer has a spectrum of activity similar to chlorpromazine, a known substance having neuroleptic and central depressant activity.

The test procedures used for the aforementioned determination of the activity or side effects are briefly described hereinafter:

NEUROLEPTIC ACTIVITY

Determination of homovanillic acid.

Rats are injected with the test substance 2 hours before they are sacrificed. Homovanillic acid is extracted from the supernatant of the brain homogenate into butyl acetate and later into an aqueous solution and oxidized with potassium ferricyanide to a fluorescent dimer. From the increased concentration of homovanillic acid (HVA) it can be concluded that the substance has neuroleptic activity, that is, it increases the turnover of dopamine in the basal ganglia. The homovanillic acid titre in untreated rats is arbitrarily fixed at 100%.

CENTRAL-DEPRESSANT ACTIVITY

Rotating rod test.

In the rotating rod test, the ability of mice to achieve a coordinated motor performance is examined. After peroral administration of the substance to be tested, mice are placed on a horizontal and slowly rotating rod and the time the mice remained on the rod is recorded. The ED 50 is the dose which reduces the retention time, that is, the time they remain off the rod, by 50% with respect to that before administration of the substance.

SIDE EFFECTS

I. Catalepsy test

Cataleptic activity, as demonstrated by "wax rigidity", that is, abnormally long retention of a fixed body position, in the case of central depressant or neuroleptically-active compounds is considered to be an undersirable side effect and is produced by motor disorders. The substance to be tested is administered intrapertioneally to rats. The animals are considered to be cataleptic when the homolateral extremities remain in a crossed position for at least 10 seconds. The number of cateleptic animals is noted every 30 minutes for 6 hours. The ED 50 is the dose at which 50% of the animals show catalepsy.

II. Toxicity

Groups of 4 mice per dosage are treated perorally with increasing amounts of the test substance. The mortality is ascertained after 24 hours and after 10 days and the dosage at which 50% of the animals survive is calculated (LD 50).

The (+)-(S)-enantiomer of formula I and its pharmaceutically acceptable acid additional salts can be used as medicaments, for example, in the form of pharmaceutical preparations which contain them in association with a compatible pharmaceutical carrrier material. Such carrier material can be an organic or inorganic inert material suitable for enteral, for example, oral or parenteral administration, for example, water, gelatin, lactose, starch, magnesium stearate, talc, vegetable oils, gum arabic, polyalkyleneglycols, or the like. The pharmaceutical preparations can be made up in a solid form, for example, as tablets, dragees, suppositories or capsules, or in a liquid form, for example, as solutions, suspensions or emulsions. If necessary, the pharmaceutical preparations can be sterilized and/or can contain adjuvants such as preserving stabilizing, wetting or emulsifying agents, including salts for varying the osmotic pressure or buffers. The pharmaceutical preparations can also contain still other therapeutically valuable substances.

Conveniently, a pharmaceutical dosage form can contain from about 1 mg. to 200 mg. of the (+)-(S)-enantiomer of formula I or an equivalent amount of a pharmaceutically acceptable acid addition salt thereof. A convenient oral dosage range comprises from about 0.1 mg/kg per day to about 10 mg/kg per day. A convenient parenteral dosage range comprises from about 0.01 mg/kg per day to about 1.0 mg/kg per day. However, the foregoing ranges can be varied upwards or downwards depending upon individual requirements and the directions of the physician administering the (+)-(S)-enantiomer of formula I, or a pharmaceutically acceptable acid addition salt thereof.

The term "lower alkyl" as used hereinabove preferably relates to straight-chain or branched groups having up to 4 carbon atoms, such as methyl, ethyl, n-propyl, isopropyl, n-butyl, isobutyl and sec-butyl.

The Examples which follow further illustrate the invention. All temperatures are in degrees Centigrade, unless otherwise mentioned.

EXAMPLE 1

Preparation of (+)-(S)-3-{2-[4-(8-fluoro-10,11-dihydro-2-methyl-dibenzo[b,f]thiepin-10-yl)-1-piperazinyl]-ethyl}-2-oxazolidinone 7.4 G. of the salt of racemic 3-{2-[4-(8-fluoro-10,11-dihydro-2-methyl-dibenzo[b,f]thiepin-10-yl)-1-piperazinyl]-ethyl}-2-oxazolidinone with (−)-di-O-benzoyl-tartaric acid monohydrate [(−)-(R,R)-2,3-dibenzoyloxy-succinic acid monohydrate; $\alpha_{546} = -132°$ (ethanol; c = 5%)] in the molar ratio of 1:1 are dissolved in 325 ml. of acetone and, after stirring for 36 hours at room temperature, the mixture is filtered. The filter cake is washed with acetone and dried under reduced pressure. After liberation of the base by treatment with aqueous sodium hydroxide, there is obtained (+)-(S)-3-{2-[4-(8-fluoro-10,11-dihydro-2-methyl-dibenzo[b,f]thiepin-10-yl)-1-piperazinyl]-ethyl}-2-oxazolidinone as crystals. The first crystallizate is obtained in a purity of 80% and in a yield of 35.2% based on the racemate used. This corresponds to a yield of 2 × 35.2% = 70.4% of the theoretically possible amount of the (+)-(S)-enantiomer. $\alpha_D = +8.0°$ (chloroform; c = 3.0%).

The racemic 3-{2-[4-(8-fluoro-10,11-dihydro-2-methyl-dibenzo[b,f]thiepin-10-yl)-1-piperazinyl]-ethyl}-2-oxazolidinone used as the starting material can be prepared as follows:

A solution of 474.5 g. of potassium hydroxide in 3.6 liters of water is treated under an atmosphere of nitrogen at 50° C. with 217 ml. of 4-fluoro-thiophenol and the mixture is stirred at room temperature for 15 minutes. After the addition of several grams of copper powder and of 536 g. of 2-iodo-5-methyl-benzoic acid, the mixture is heated under reflux for 7 hours. The mixture is filtered while hot, acidified with concentrated hydrochloric acid and again filtered. The residue is washed neutral with water and dried under reduced pressure, and there is obtained 3-methyl-6-[(4'-fluoro-phenyl)-thio]-benzoic acid of melting point 166°–167° C.

300 G. of 3-methyl-6-[(4'-fluoro-phenyl)-thio]-benzoic acid in 2 liters of absolute tetrahydrofuran are treated dropwise under an atmosphere of nitrogen and under reflux with 780 ml. of a 70% sodium dihydro-bis(2-methoxy-ethoxy)-aluminate solution in benzene and heated under reflux for an additional hour. The mixture is cooled to 4° C., acidified dropwise with 1300 ml. of 3N hydrochloric acid, treated with concentrated hydrochloric acid and extracted with benzene. The organic phase is washed with water, dried over sodium sulfate, filtered and evaporated, whereby there is obtained 3-methyl-6-[(4'-fluoro-phenyl)-thio]-benzyl alcohol as a yellow oil.

337 G. of 3-methyl-6-[(4'-fluoro-phenyl)-thio]-benzyl alcohol are dissolved in 1 liter of absolute benzene and brought to reflux temperature. The solution is treated dropwise with 190 ml. of thionyl chloride and boiled for an additional 45 minutes. The mixture is evaporated under reduced pressure. The residue is extracted several times with benzene. The benzene extracts are evaporated, and there is obtained 3-methyl-6-[(4'-fluoro-phenyl)-thio]-benzyl chloride as a brown oil.

115 G. of potassium cyanide in 150 ml. of water are heated under reflux for 10 hours with 344 g. of 3-methyl-6-[(4'-fluoro-phenyl)-thio]-benzyl chloride in 450 ml. of ethanol. The ethanol is subsequently removed by distillation under reduced pressure. The residue is diluted with water and extracted with benzene. The benzene phase is washed with water, dried over sodium sulfate and evaporated, and there is obtained 3-methyl-6-[(4'-fluorophenyl)-thiol]-phenylacetonitrile as a dark-brown oil.

106 G. of 3-methyl-6-[(4'-fluoro-phenyl)-thio]-phenylacetonitrile, 300 ml. of ethanol, 100 g. of potassium hydroxide and 300 ml. of water are heated under reflux for 5 hours. The ethanol is subsequently removed by evaporation under reduced pressure. The residue is dissolved in water and the neutral constituents extracted with benzene. The aqueous solution is acidified with concentrated hydrochloric acid and extracted with ethyl acetate. The organic phase is washed with water, dried over sodium sulfate, filtered and evaporated under reduced pressure, and there is obtained 3-methyl-6-[(4'-fluoro-phenyl)-thio]-phenyl-acetic acid as a dark-brown oil which, after recrystallization from benzene hexane, forms crystals melting at 117° C.

1810 G. of polyphosphoric acid are heated to 128° C. under an atmosphere of nitrogen, rapidly treated with 173.6 g. of 3-methyl-6-[(4'-fluoro-phenyl)-thio]-phenylacetic acid and stirred at 120°–130° C. for 10 minutes. After the addition of ice chips, the entire mixture is extracted with benzene. The organic phase is washed with water and with a saturated aqueous sodium carbonate solution, dried over sodium sulfate and evaporated, and there is obtained 8-fluoro-2-methyl-dibenzo[b,f]thiepin-10(11H)-one which melts at 103°–104° C.

103 G. of 8-fluoro-2-methyl-dibenzo[b,f]thiepin-10(11H)-one are suspended in 550 ml. of ethanol and treated with 24.3 g. of sodium borohydride. The mixture is heated under reflux for about 10 minutes. After the addition of water, the mixture is extracted with chloroform. The organic phase is washed with water, dried over sodium sulfate and evaporated, and there is obtained racemic 8-fluoro-10,11-dihydro-2-methyl-dibenzo[b,f]thiepin-10ol as an oil.

103 G. of racemic 8-fluoro-10,11-dihydro-2-methyl-dibenzo[b,f]thiepin-10-ol, 500 ml. of benzene and 38.4 g. of finely powdered calcium chloride are saturated with hydrochloric acid gas at 15° C. and stirred overnight. The precipitate is removed by filtration, washed with benzene and evaporated under reduced pressure, and there is obtained racemic 10-chloro-8-fluoro-10,11-dihydro-2-methyl-dibenzo[b,f]thiepin which melts at 63°–64° C.

29 G. of racemic 10-chloro-8-fluoro-10,11-dihydro-2-methyl-dibenzo[b,f]-thiepin in 130 ml. of chloroform are heated under reflux for 20 hours with 45 g. of 3-[2-(1-piperazinyl)-ethyl]-2-oxazolidinone. The chloroform is removed by evaporation, the residue dissolved in 3N methanesulfonic acid and ethyl acetate, the methanesulfonic acid phase made alkaline with concentrated aqueous sodium hydroxide and the precipitated base taken up in chloroform. For purification, the chloroform phase is chromatographed over neutral aluminum oxide (activity grade III). The racemic 3-{2-[4-(8-fluoro-10,11-dihydro-2-methyl-dibenzo[b,f]thiepin-10yl)-1-piperazinyl]-ethyl}-2-oxazolidinone which is eluted with chloroform is recrystallized from ethanol and melts at 175°–176° C.

EXAMPLE 2

Preparation of (−)-(R)-3-{2-[4-(8-fluoro-10,11-dihydro-2-methyl-dibenzo[b,f]-thiepin-10yl)-1-piperazinyl]-ethyl}-2-oxazolidinone If, in Example 1, 312 ml. of ethanol are used as the solvent in place of acetone, then there is obtained, after stirring for 36 hours at room temperature and liberation of the base with aqueous sodium hydroxide, (−)-(R)-3-{2-[4-(8-fluoro-10,11-dihydro-2-methyl-dibenzo[b,f]-thiepin-10-yl)-1-piperazinyl]-ethyl}-2-oxazolidinone as crystals. The first crystallizate is obtained in a purity of about 87% and in a yield of about 40% based on the racemate used (that is, about 80% of theory). $\alpha_D = 10.4°$ (chloroform; c = 2%).

EXAMPLE 3

Preparation of di-(camphor-10-sulfonic acid) salt of (+)-(S)-3-{2-[4-(8-fluoro-10,11-dihydro-2-methyl-dibenzo[b,f]thiepin-10-yl)-1-piperazinyl]-ethyl}-2-oxazolidinone 3 G. of the salt of racemic 3-{2-[4-(8-fluoro-10,11-dihydro-2-methyldibenzo[b,f]thiepin-10-yl)-1-piperazinyl]-ethyl}-2-oxazolidinone with (+)-camphor-10-sulfonic acid monohydrate [(S)-2-oxo-10-bornanesulfonic acid; $\alpha_{546} = +28.0°$ (water; c = 10%)] in the molar ratio of 1:2 are dissolved in 5 ml. of acetone and allowed to stand at room temperature for 2 hours. After the addition of 5 ml. of acetone, the entire mixture is allowed to stand for an additional 2 hours and then treated with 3 ml. of acetone. The solution is now left to stand at room temperature for 85 hours. The precipitate obtained is subsequently removed by filtration and washed with acetone, and there is obtained the di(camphor-10-sulfonic acid) salt of (+)-(S)-3-{2-[4-(8-fluoro-10,11-dihydro-2-methyl-dibenzo[b,f]thiepin-10-yl)-1-piperazinyl]-ethyl}-2-oxazolidinone [that is, (+)-(S)-3-{2-[4-(8-fluoro-10,11-dihydro-2-methyl-dibenzo[b,f]-thiepin-10-yl)-1-piperazinyl]-ethyl}-2-oxazolidinone-(S)-2-oxo-10-bornanesulfonate (1:2)], from which the base is liberated by treatment with aqueous sodium hydroxide. The first crystallizate is obtained in a purity of about 84% and in a yield of 23.3% based on the racemate used (that is, 46.6% of theory). $\alpha_D = +9.5°$ (chloroform; c = 1%).

EXAMPLE 4

Preparation of (+)-(S)-3-{2-[4-(8-fluoro-10,11-dihydro-2-methyl-dibenzo[b,f]thiepin-10-yl)-1-piperazinyl]-ethyl}-2-oxazolidinone 20 G. of racemic 3-{2-[4-(8-fluoro-10,11-dihydro-2-methyl-dibenzo[b,f]thiepin-10-yl)-1-piperazinyl]-ethyl}-2-oxazolidinone are maintained at reflux with stirring together with 22.6 g. of (+)-camphor-10-sulfonic acid monohydrate [(S)-2-oxo-bornanesulfonic acid monohydrate; $\alpha_{546} = +28.0°$ (water; c = 10%)] and 350 ml. of acetone and seeded with a small amount of the di-(camphor-10-sulfonic acid) salt of (+)-(S)-3-{2-[4-(8-fluoro-10,11-dihydro-2-methyl-dibenzo-[b,f]thiepin-10-yl)-1-piperazinyl]-ethyl}-2-oxazolidinone. The mixture is maintained at reflux with stirring for 72 hours. The precipitate obtained is removed by filtration, washed with acetone and dried under reduced pressure, and there is obtained pure white di-(camphor-10-sulfonic acid) salt of (+)-(S)-3-{2-[4-(8-fluoro-10,11-dihydro-2-methyl-dibenzo[b,f]thiepin-10-yl)-1-piperazinyl]-ethyl}-2-oxazolidinone [that is, (+)-(S)-3-{2-[4-(8-fluoro-10,11-dihydro-2-methyl-dibenzo[b,f]thiepin-10-yl)-1-piperazinyl]-ethyl}-2-oxazolidinone-(S)-2-oxo-10-bornanesulfonate (1:2)], $\alpha_D = +23.6°$, $\alpha_{364} = +78.2°$ (dimethylformamide; c = 3.0%); melting point 94° C. (decomposition). The lower melting point is due to the amorphous crystalline nature of the product.

The foregoing precedure is repeated using 100 g. of racemic 3-{2-[4-(8-fluoro-10,11-dihydro-2-methyl-dibenzo[b,f]thiepin-10-yl)-1-piperazinyl]-ethyl }-2-oxazolidinone, 113.2 g. of (+)-camphor-10-sulfonic acid monohydrate and 300 ml. of acetone. The stirring under reflux is carried out for 24 hours in place of 72 hours, and the drying under reduced pressure is prolonged. Whereupon, there is obtained the di-(camphor-10-sulfonic acid) salt of (+)-(S)-3-{2-[4-(8-fluoro-10,11-dihydro-2-methyl-dibenzo[b,f]thiepin-10-yl)-1-piperazinyl]-ethyl}-2-oxazolidinone; $\alpha_D = +14.9°$, $\alpha_{364} = +104.0°$ (chloroform; c = 3.0%); melting point 174°–175° C. (after recrystallization from acetone).

To liberate the base, the salt obtained is chromatographed on aluminum oxide of activity grade I (basic) with chloroform/ethanol (9:1). The eluted (+)-(S)-3-{2-[4-(8-fluoro-10,11-dihydro-2-methyl-dibenzo[b,f]-thiepin-10-yl)-1-piperazinyl]-ethyl}-2-oxazolidinone is recrystallized from ethanol. The thus-obtained product, which is practically 100% pure, melts at 170°–170.5° C.; $\alpha_D = +13.6°$; $\alpha_{365} = -182.0°$ (chloroform; C = 2.5%). The yield is 35.2% based on the racemate (that is, 60.4% of theory).

The corresponding dimethanesulfonate or maleate is prepared by treating this base with methanesulfonic acid or maleic acid, respectively.

EXAMPLE 5

Preparation of (R)-3-{2-[4-(8-fluoro-10,11-dihydro-2-methyl-dibenzo[b,f]thiepin-10-yl)-1-piperazinyl]-ethyl}-2-oxazolidinone 5.0 G. of the salt of racemic 3-{2-[4-(8-fluoro-10,11-dihydro-2-methyl-dibenzo[b,f]thiepin-10-yl)-1-piperazinyl]-ethyl}-2-oxazolidinone with (+)-(R,R)-tartaric acid [$\alpha_{546} = +15.0°$ (water; c = 10%)] in the molar ratio of 1:1 are dissolved in 500 ml. of acetone and, after stirring for 24 hours at room temperature, the mixture is filtered. The filter cake is washed with acetone, dried under reduced pressure, and there is obtained 3-[2-{4-[(R)-8-fluoro-10,11-dihydro-2-methyl-dibenzo[b,f]thiepin-10-yl}-1-piperazinyl]-ethyl]-2-oxazolidinone-(R,R)-tartrate (1:1); $\alpha_{365} = +98.6°$ (dimethylformamide; c = 2.0%); decomposition point 172° C. After liberation of the base by treatment with aqueous sodium hydroxide, there is obtained crystalline (R)-3-{2-[4-(8-fluoro-10,11-dihydro-2-methyl-dibenzo[b,f]thiepin-10-yl)-1-piperazinyl]-ethyl}-2-oxazolidinone; $\alpha_{365} = +183.85°$ (chloroform; c = 0.5%) in a purity above 99%. The yield amounts to 54.4% of theory.

EXAMPLE 6

Preparation of (S)-3-{2-[4-(8-fluoro-10,11-dihydro-2-methyl-dibenzo[b,f]thiepin-10-yl)-1-piperazinyl]-ethyl}-2-oxazolidinone-2,3-di-O-(p-toluoyl)-(S,S)-tartrate 4.22 G. of the salt of racemic 3-{2-[4-(8-fluoro-10,11-dihydro-2-methyl-dibenzo[b,f]thiepin-10-yl)-1-piperazinyl]-ethyl}-2-oxazolidinone with (+)-(S,S)-di-O-(p-toluoyl)-tartaric acid [$\alpha_{546} = +165°$ (ethanol; c = 1.0%)] in the molar ratio of 1:1 are dissolved in 225 ml. of absolute methanol and stirred at room temperature. The precipitated salt is removed by filtration, washed with methanol and dried under reduced pressure, and there is obtained pure (S)-3-{2-[4-(8-fluoro-10,11-dihydro-2-methyl-dibenzo[b,f]thiepin-10-yl)-1-piperazinyl]-ethyl }-2-oxazolidinone-2,3-di-O-(p-toluoyl)-(S,S)-tartrate (1:1); $\alpha_{365} = +31.6°$ (chloroform; c = 2.00%). The yield amounts to 81.8% of theory.

EXAMPLE 7

Preparation of 3-[2-{4-[(S)-8-fluoro-10,11-dihydro-2-methyl-dibenzo[b,f]thiepin-10-yl}-1-piperazinyl]-ethyl]-2-oxazolidinone-(S)-(+)-4-hydroxydinaphtho[2,1-d;1',2'-f][1,3,2]dioxaphosphepin-4-oxide 6.76 G. of the salt of racemic 3-{2-[4-(8-fluoro-10,11-dihydro-2-methyl-dibenzo[b,f]thiepin-10yl)-1-piperazinyl]-ethyl}-2-oxazolidinone with (+)-(S)-2,2'-(1,1'-dinaphthyl)-phosphoric acid [$\alpha_D = +617°$ (methanol; c = 1.0%)] in the molar ratio of 1:2 are dissolved in 1140 ml. of absolute ethanol. The slightly yellow solution is preferably seeded with a small amount of 3-[2-{4-[(S)-8-fluoro-10,11-dihydro-2-methyl-dibenzo[b,f]thiepin-10-yl}-1-piperazinyl]-ethyl]-2-oxazolidinone-(S)-(+)-4-hydroxydinaphtho[2,1-d:1',2'-f][1,3,2]-dioxaphosphepin-4-oxide (1:2). The mixture is stirred for 24 hours. The crystallizate obtained is removed by filtration and washed with ethanol, and there is obtained 3-[2-{4-[(S)-8-fluoro-10,11-dihydro-2-methyl-dibenzo[b,f]thiepin-10-yl}-1-piperazinyl]-ethyl]-2-oxazolidinone-(S)-(+)-4-hydroxydinaphtho[2,1-d:1',2'-f][1,3,2]dioxaphosphepin-4-oxide (1:2). $\alpha_D = +349.32°$; $\alpha_{365} = +949.3°$ (dimethylformamide; c = 2.0%); melting point/decomposition point 212° C. The yield amounts to 59.0% of theory.

EXAMPLE 8

Preparation of (R)-3-{2-[4-(8-fluoro-10,11-dihydro-2-methyl-dibenzo[b,f]thiepin-10-yl)-1-piperazinyl]-ethyl}-2-oxazolidinone-(R)-2-oxo-10-bornanesulfonate 4.52 G. of the salt of racemic 3-{2-[4-(8-fluoro-10,11-dihydro-2-methyl-dibenzo[b,f]thiepin-10-yl)-1-piperazinyl]-ethyl}-2-oxazolidinone with (-)-(R)-2-oxo-10-bornanesulfonic acid [$\alpha_D = -20.2°$, $\alpha_{546} = -26.7°$ (water; c = 5.40%)] in the molar ratio of 1:2 are dissolved in 55 ml. of ethanol and seeded at 40° C. with (R)-3-{2-[4-(8-fluoro-10,11-dihydro-2-methyl-dibenzo[b,f]thiepin-10-yl)-1-piperazinyl]-ethyl}-2-oxazolidinone-(R)-2-oxo-10-bornanesulfonate (1:2). After stirring for 48 hours at room temperature, the mixture is filtered. The filter cake is washed with ethanol and dried under reduced pressure, and there is obtained (R)-3-{2-[4-(8-fluoro-10,11-dihydro-2-methyl-dibenzo[b,f]thiepin-10yl)-1-piperazinyl]-ethyl}-2-oxazolidinone-(R)-2-oxo-10-bornanesulfonate (1:2); $\alpha_D = -15.7°$; $\alpha_{365} = -112.3°$ (chloroform; c = 2.50%). The yield amounts to about 50% of theory and the product is about 90% pure.

EXAMPLE 9

Preparation of (S)-3-{2-[4-(8-fluoro-10,11-dihydro-2-methyl-dibenzo[b,f]thiepin-10yl)-1-piperazinyl]-ethyl}-2-oxazolidinone 5 G. of the salt of racemic 3-{2-[4-(8-fluoro-10,11-dihydro-2-methyl-dibenzo[b,f]thiepin-10-yl)-1-piperazinyl]-ethyl}-2-oxazolidinone with (+)-(S)-3-endo-bromo-2-oxo-10-bornanesulfonic acid [$\alpha_D = +92.3°$; $\alpha_{365} = +554.2°$; $\alpha_{436} = +231.5°$ (water; c = 0.60%)] in the molar ratio of 1:2 are dissolved in 100 ml. of ethanol and preferably seeded with a small amount of 3-[2-{4-[(S)-8-fluoro-10,11-dihydro-2-methyl-dibenzo[b,f]thiepin-10-yl]-1-piperazinyl} -ethyl]-2-oxazolidinone-(S)-3-endo-bromo-2-oxo-10-bornanesulfonate (1:2). After stirring for 48 hours at room temperature, the salt which crystallizes out is removed by filtration. The filter cake is washed with acetone and dried under reduced pressure, and there is obtained 3-[2-{4-[(S)-8-fluoro-10,11-dihydro-2-methyl-dibenzo[b,f]thiepin-10-yl]-1-piperazinyl}-ethyl]-2-oxazolidinone-(S)-3-endo-bromo-2-oxo-10-bornanesulfonate (1:2); $\alpha_D = +71.2°$; $\alpha_{365} = +358.0°$ (dimethylformamide; c = 2.0%); melting point/decomposition point 134° C.

After liberation of the base on aluminum oxide of activity grade I (basic) with chloroform/ethanol (9:1), there is obtained (S)-3-{2-[4-(8-fluoro-10,11-dihydro-2-methyl-dibenzo[b,f]thiepin-10-yl)-1-piperazinyl]-ethyl}-2-oxazolidinone; $\alpha_D = 182.5°$ (chloroform, c = 0.50%); melting point 179° C. The yield amounts to 15.3% of theory and the product is obtained in a purity of about 96%.

EXAMPLE 10

Preparation of (S)-3-{2-[4-(8-fluoro-10,11-dihydro-2-methyl-dibenzo[b,f]thiepin-10-yl)-1-piperazinyl]-ethyl}-2-oxazolidinone 6.13 G. of the salt of racemic 3-}2-[4-(8-fluoro-10,11-dihydro-2-methyldibenzo[b,f]thiepin-10-yl)-1-piperazinyl]-ethyl}-2-oxazolidinone with (+)-(R)-3-endo-bromo-2-oxo-8-bornanesulfonic acid [$\alpha_D = +81.7°$; $\alpha_{436} = +218.4°$ (water; c = 2.0%)] in the molar ratio of 1:2 are dissolved in 287 ml. of ethanol, preferably seeded with 3-[2-{4-[(S)-8-fluoro-10,11-dihydro-2-methyl-dibenzo[b,f]thiepin-10-yl}-1-piperazinyl]-ethyl]-2-oxazolidinone-(R)-3-endo-bromo-2-oxo-8-bornanesulfonate (1:2) and, after stirring for 24 hours at room temperature, the mixture is filtered. The diastereomeric salt is washed and dried under reduced pressure, and there is obtained pure 3-[2-{4-[(S)-8-fluoro-10,11-dihydro-2-methyl-dibenzo[b,f]thiepin-10-yl}-1-piperazinyl]-ethyl}-2-oxazolidinone-(R)-3-endo-bromo-2-oxo-8-bornanesulfonate (1:2); $\alpha_{365} = +491.3°$ (dimethylformamide; c = 2.00%); decomposition from 187° C.

After liberation of the base by treatment with aqueous sodium hydroxide and recrystallization from ethanol, there is obtained pure (S)-3-{2-[4-(8-fluoro-10,11-dihydro-2-methyl-dibenzo[b,f]thiepin-10-yl)-1-piperazinyl]-ethyl}-2-oxazolidinone; $\alpha_D = +12.4°$; $\alpha_{365} = -186.7°$ (chloroform; c = 0.498%); melting point 168.5°-169.5° C. The yield amounts to 69.5% of theory.

EXAMPLE 11

Preparation of (+)-(S)-3-{2-[4-(8-fluoro-10,11-dihydro-2-methyl-dibenzo[b,f]thiepin-10-yl)-1-piperazinyl]-ethyl}-2-oxazolidinone 10 G. of racemic 3-{2-[4-(8-fluoro-10,11-dihydro-2-methyl-dibenzo[b,f]thiepin-10-yl)-1-piperazinyl]-ethyl}-2-oxazolidinone are maintained at reflux with stirring together with 11.3 g. of (+)-camphor-10-sulfonic acid monohydrate [$\alpha_{546} = +28.0°$ (water; c = 10%)] and 130 ml. of methyl ethyl ketone and the mixture is preferably seeded with a small amount of (+)-3-[2-{4-[(S)-8-fluoro-10,11-dihydro-2-methyl-dibenzo[b,f]thiepin-10-yl}-1-piperazinyl]-ethyl]-2-oxazolidinone-(S)-2-oxo-10-bornanesulfonate (1:2). An additional 70 ml. of methyl ethyl ketone are added after 3 hours. The mixture is maintained at reflux with stirring for 20 hours. The precipitate obtained is removed by filtration, washed with methyl ethyl ketone and dried under reduced pressure, and there is obtained white (+)-3-{2-[4-(8-fluoro-10,11-dihydro-2-methyldibenzo[b,f]thiepin-10-yl)-1-piperazinyl]-ethyl}-2-oxazolidinone-(S)-2-oxo-10-bornanesulfonate (1:2); $\alpha_D = +14.1°$; $\alpha_{365} = +102°$ (chloroform; c = 3.0%); melting point 164°-166° C.

To liberate the base, the salt obtained is chromatographed on aluminum oxide of activity grade I (basic with chloroform/ethanol (9:1). The eluted (+)-(S)-3-{2-[4-(8-fluoro-10,11-dihydro-2-methyl-dibenzo[b,f]thiepin-10yl)-1-piperazinyl]-ethyl}-2-oxazolidinone is recrystallized from ethanol. The product, which is obtained in a purity of 96%, melts at 167.5°-169.9° C.; $\alpha_D = +12.9°$; $\alpha_{365} = -168.9°$ (chloroform; c = 2.5%). The yield amounts to 41% based on the racemate, that is, 82% of theory.

EXAMPLE 12

Preparation of (+)-(S)-3-{2-[4-(8-fluoro-10,11-dihydro-2-methyl-dibenzo[b,f]thiepin-10-yl)-1-piperazinyl]-ethyl}-2-oxazolidinone 0.59 G. of enriched (+)-(S)-1-(8-fluoro-10,11-dihydro-2-methyl-dibenzo-[b,f]thiepin-10-yl)-piperazine [$\alpha_D = +30.8°$; $\alpha_{546} = +30.8°$ (chloroform; c = 2.50%) together with 0.47 g. of powdered potassium carbonate, 0.033 g. of potassium iodide and 4 ml. of toluene are treated with 0.64 g. of 3-(2-chloro-ethyl)-2-oxazolidinone and heated under reflux for 20 hours with stirring. The mixture is poured on to water and diluted with benzene. The organic phase is washed with water and dilute sodium chloride solution, dried over sodium sulfate and evaporated. The benzene extract is chromatographed on aluminum oxide of activity grade III (neutral). The eluted (+)-(S)-3-{2-[4-(8-fluoro-10,11-dihydro-2-methyl-dibenzo[b,f]thiepin-10-yl)-1-piperazinyl]-ethyl}-2-oxazolidinone; $\alpha_D = +10.0°$; $\alpha_{365} = -132.8°$ (chloroform, c = 2.50%) can be further purified by treatment with (+)-(S)-2-oxo-10-bornanesulfonic acid in acetone in the same manner as described in Example 4, whereupon, there is obtained(+)-3-[2-{4-[(S)-8-fluoro-10,11-dihyrdo-2-methyl-dibenzo[b,f]thiepin-10-yl]-1-piperazinyl}-ethyl]-2-oxazolidinone-(S)-2-oxo-10-bornanesulfonate (1:2) from which the base can be liberated on aluminum oxide of activity grade I (basic). The eluted pure (+)-(S)-3-{2-[4-(8-fluoro-10,11-dihydro-2-methyl-dibenzo[b,f]thiepin-10-yl)-1-piperazinyl]ethyl}-2-oxazolidinone is recrystallized from ethanol. The pure product obtained melts at 170.5° C; $\alpha_D = +13.2°$; $\alpha_{365} = -180.6°$ (chloroform; c = 0.50%).

The enriched (+)-(S)-1-(8-fluoro-10,11-dihydro-2-methyl-dibenzo[b,f]thiepin-10-yl)-piperazine used as the starting material can be prepared as follows:

71 G. of racemic 10-chloro-8-fluoro-10,11-dihydro-2-methyl-dibenzo-[b,f]thiepin in 95 ml. of chloroform are heated under reflux for 60 hours with 89 ml. of 1-carbethoxy-piperazine. The mixture is poured on to ice-water and extraceted with ether. The organic phase is dried over sodium sulfate and evaporated under reduced pressure, and there is obtained crude oily 1-carbethoxy-4-(8-fluoro-10,11-dihydro-2-methyl-dibenzo[b,f]thiepin-10-yl)-piperazine 106.5 G. of 1-carbethoxy-4-(8-fluoro-10,11-dihydro-2-methyl-dibenzo-[b,f]thiepin-10-yl)piperazine, 915 ml. of ethyleneglycol, 38.3 g. of potassium hydroxide and 4.1 ml. of water are heated to 160° C. for 7 hours. The mixture is poured on to water and extracted with ether. The organic phase is washed with 0.5-M aqueous methanesulfonic acid. The aqueous methanesulfonic acid solution is made alkaline with aqueous ammonia and extracted with benzene. The benzene extract obtained is purified by chromatography on aluminum oxide of activity grade I (basic) with benzene, chloroform and ethanol. For further purification, the eluted racemic 1-(8-fluoro-10,11-dihydro-2-methyl-dibenzo-[b,f]thiepin-10-yl)-piperazine is converted three times into the corresponding dihydrochloride using ethanolic hydrochloric acid and ether. The pure base of the racemic 1-(8-fluoro-10,11-dihydro-2-methyl-dibenzo[b,f]thiepin-10-yl)piperazine, which is recrystallized from n-hexane, melts at 80°-82° C.

0.94 G. of the salt of racemic 1-(8-fluoro-10,11-dihydro-2methyl-dibenzo-[b,f]thiepin-10-yl)-piperazine with 2,3:4,6-di-O-isopropylidene- α-L-xylo2-hexulofuranosonic acid monohydrate [$\alpha_D = -20.0°$ (methanol; c = 2.0%)]in the molar ratio of 1:1 are dissolved in 68 ml. of methanol and left to stand at room temperature for 196 hours. The mixture is then stirred for 140 hours and subsequently filtered. The precipitate obtained is removed by filtration, washed with methanol and dried under reduced pressure, and there is obtained the enriched white 2,3:4,6-di-O-isopropylidene- α -L-xylo-2-hexulofuranosonate salt of (R)-1-(8-fluoro-10,11-dihydro-2-methyl-dibenzo[b,f]thiepin-10-yl)-piperazine; $\alpha_D = -6.3°$; $\alpha_{436} = +14.8°$; $\alpha_{305} = +117.8°$ (methanol; c = 0.20%); melting point 262° C. (decomposition).

The procedure described earlier is repeated using 367 ml. of ethanol in place of the methanol. In addition, the solution is seeded with a small amount of the 2,3:4,6-di-O-isopropylidene- α -L-xylo-2-hexulofuranosonate salt of (R)-1-(8-fluoro-10,11-dihydro-2-methyl-dibenzo[b,f]thiepin-10-yl)-piperazine. After stirring at room temperature for 192 hours, the mixture is filtered, the filter cake washed with ethanol and dried under reduced pressure, whereupon, there is obtained in the enriched white 2,3:4,6-di-O-isopropylidene- α -L-xylo-2-hexulofuranosonate salt of (R)-1-(8-fluoro-10,11-dihydro-2-methyl-dibenzo[b,f]thiepin-10-yl)-piperazine; $\alpha_D = -5.5°$; $\alpha_{436} = +14.1°$; $\alpha_{365} = +113.2°$ (methanol; c = 0.20%); melting point 262° C. (decomposition).

35.3 G. of the salt of racemic 1-(8-fluoro-10,11-dihydro-2-methyldibenzo[b,f]thiepin-10-yl)-piperazine with 2,3:4,6-di-O-isopropylidene-α -L-xylo-2-hexulofuranosonic acid monohydrate [$\alpha_D = -20.2°$ (methanol; c = 2.0%)] in the molar ratio of 1:1 are dissolved in 2800 ml. of absolute methanol and seeded with a small amount of the 2,3:4,6-di-O-isopropylidene-α -L-xylo-2-hexulofuranosonate salt of (R)-1-(8-fluoro-10,11-dihydro-2-methyl-dibenzo[b,f]thiepin-10-yl)-piperazine. The mixture is stirred at room temperature for 26 hours. The first precipitate obtained is removed by filtration, washed with methanol and dried under reduced pressure, and there is obtained the white 2,3:4,6-di-O-isopropylidene-α -L-xylo-2-hexulofuranosonate salt of (R)-1-(8-fluoro-10,11-dihydro-2-methyl-dibenzo[b,f]thiepin-10-yl)-piperazine; $\alpha_D = -6.5°$; $\alpha_{436} = +15.0°$; $\alpha_{365} = +118.5°$ methanol; c = 0.20%); melting point 259° C (decomposition).

If the salt obtained is recrystallized from methanol, its optical rotation values are $\alpha_D = -5.5°$; $\alpha_{430} = +18.0°$; $\alpha_{365} = +123.5°$ (methanol; c = 0.20%) and its melting point is 262° C (decomposition).

From the filtrate of the optical splitting there can be isolated by increasing the concentration of the diastereomeric salts from 2.2% or 2.7% (evaporation of the methanol) an additional two portions of the 2,3:4,6-di-O-isopropylidene-α -L-xylo-2-hexulofuranosonate salt of (R)-1-(8-fluoro-10,11-dihydro-2-methyldibenzo[b,f]-thiepin-10-yl)-piperazine.

Portion 2: $\alpha_D = -6.5°$; $\alpha_{436} = +13.0°$; $\alpha_{365} = +107.5°$ (methanol; c = 0.20%).

rortion 3: $\alpha_D = -6.5°$; $\alpha_{436} = +10.5°$; $\alpha_{365} = +99.5°$ (methanol; c = 0.20%).

The yield of the crystallized diastereomeric salt amounts to 83.8% of theory.

In order to liberate the free base, the resulting enriched (S)-1-(8-fluoro-10,11-dihydro-2-methyl-dibenzo[b,f]thiepin-10-yl)-piperazine-2,3:4,6-di-O-isopropylidene- α-L-xylo-2-hexulofuranosonate is dissolved in 0.5-M aqueous methanesulfonic acid, treated with ammonia and extracted with benzene. The organic phase is washed with water, dried over sodium sulfate and evaporated, and there is obtained oily (+)-(S)-1-(8-fluoro-10,11-dihydro-2-methyl-dibenzo[b,f]thiepin-10-yl)-piperazine; $\alpha_D = +30.8°$; $\alpha_{436} = +30.8°$ (chloroform; c = 2.50%).

3.47 G. of (+)-(S)-1-(8-fluoro-10,11-dihydro-2-methyl-dibenzo[b,f]thiepin-10-yl)-piperazine from the filtrate of the aforementioned three portions having the rotations $\alpha_D = +30.8°$; $\alpha_{436} = +30.8°$ (chloroform; c = 2.50%) are stirred together at room temperature for 24 hours with 3.98 g. of (−)-(R,R)-2,3-dibenzoyloxy-succinic acid monohydrate [$\alpha_{546} = -132°$ (ethanol; c = 5.0%)] and 70 ml. of ethanol. The mixture is subsequently filtered. The crystallizate is washed with ethanol and dried under reduced pressure. After repeated recrystallization from ethanol, there is obtained the 2,3-di-O-benzoyloxysuccinic acid salt of (+)-(S)-1-(8-fluoro-10,11-dihydro-2-methyl-dibenzo[b,f]thiepin-10-yl)-piperazine; $\alpha_D = -12.5°$; $\alpha_{436} = -53.5°$; $\alpha_{365} = -174.3°$ (dimethylformamide; c = 1.0%); melting point 177.5° C. (decomposition).

To liberate the base, the salt obtained by recrystallization from ethanol is treated with aqueous ammonia and extracted with benzene. The organic phase is washed with water and with aqueous sodium chloride solution, dried over sodium sulfate and evaporated, whereupon, there is obtained (+)-(S)-1-(8-fluoro-10,11-dihydro-2-methyl-dibenzo[b,f]thiepin-10-yl)-piperazine.

EXAMPLE 13

Preparation of racemic 8-fluoro-10,11-dihydro-2-methyl-dibenzo[b,f]thiepin-10-ol 5.0 G. of enriched (−)-(R)-3-{2-[4-(8-fluoro-10,11-dihydro-2-methyl-dibenzo[b,f]thiepin-10-yl)-1-piperazinyl]ethyl}-2-oxazolidinone $\alpha_D^{20} = -9.5°$; $\alpha_{365} = +125.0°$ (chloroform; c = 2.50%)] are heated under reflux for 18 hours with stirring in 81 ml. of 0.5-M methanesulfonic acid and the mixture is subsequently treated with benzene. The organic phase is washed with water, dried over sodium sulfate and evaporated. The residue is crystallized from n-hexane, and there is obtained racemic 8-fluoro-10,11-dihydro-2-methyl-dibenzo[b,f]thiepin-10-ol having a melting point of 89.5°–90° C. The yield is 97%. This compound can be converted in accordance with the procedure described in Example 1 into the 10-chloro compound which can subsequently be used in Example 1 or 11.

EXAMPLE 14

Preparation of racemic 8-fluoro-10,11-dihydro-2-methyl-dibenzo[b,f]thiepin-10-ol 2.3 G. of enriched (R)-1-(8-fluoro-10,11-dihydro-2-methyl-dibenzo[b,f]thiepin-10-yl)-piperazine [$\alpha_D = -25.0°$ (chloroform; c = 2.50%)] are heated to reflux with stirring for 24 hours in 0.57-M methanesulfonic acid and worked up in a manner analogous to that described in Example 13. For purification, the benzene extract is chromatographed on silica gel (0.2–0.5 mm) with chloroform. The eluted oily racemic 8-fluoro-10,11-dihydro-2-methyl-dibenzo[b,f]thiepin-10-ol melts at 90.5° C. after recrystallization from n-hexane.

The Examples which follow illusltrate typical pharmaceutical preparations utilizing the compounds of the invention. Any multiple of the amounts given per tablet can be conveniently utilized.

EXAMPLE A

| Tablets | Per Tablet |
|---|---|
| (+)-(S)-3-{2-[4-(8-fluoro-10,11-dihydro-2-methyl-dibenzo[b,f]thiepin-10-yl)-1-piperazinyl]-ethyl}-2-oxazolidinone | 100 mg. |
| Lactose | 202 mg. |
| Maize Starch | 80 mg. |
| Hydrolyzed Maize Starch | 20 mg. |
| Calcium Stearate | 8 mg. |
| Total Weight | 410 mg. |

The active ingredient, lactose, maize starch and hydrolyzed maize starch are mixed and granulated with water to a thick paste. This paste is passed through a sieve and subsequently dried overnight at 45° C. The dried granulate is passed through a sieve and subsequently mixed with the calcium stearate. The mixture obtained is pressed to tablets weighing 410 mg. and having a diameter of about 10 mm.

EXAMPLE B

| Tablets | Per Tablet |
|---|---|
| (+)-(S)-3-{2-[4-(8-fluoro-10,11-dihydro-2-methyl-dibenzo[b,f]thiepin-10-yl)-1-piperazinyl]ethyl}-2-oxazolidinone | 25.0 mg. |
| Lactose | 114.0 mg. |
| Maize Starch | 50.0 mg. |
| Gelatinized Maize Starch | 8.0 mg. |
| Calcium Stearate | 3.0 mg. |
| Total Weight | 200.0 mg. |

The active ingredient, lactose, maize starch and gelatinized maize starch are intimately mixed with one another. The mixture is passed through a comminuting machine and subsequently moistened with water to a thick paste. The moist mass is passed through a sieve, and the moist granulate is dried at 45° C. The dried granulate is thoroughly mixed with calcium stearate, and then the granulate is pressed to tablets weighing 200 mg. and having a diameter of about 8 mm.

EXAMPLE C

| Tablets | Per Tablet |
|---|---|
| (+)-(S)-3-{2-[4-(8-fluoro-10,11-dihydro-2-methyl-dibenzo[b,f]thiepin-10-yl)1-piperazinyl]ethyl}-2-oxazolidinone dimethanesulfonate | 14.5 mg. |
| Lactose | 124.5 mg. |
| Maize Starch | 50.0 mg. |
| Gelatinized Maize Starch | 8.0 mg. |
| Calcium Stearate | 3.0 mg. |
| Total Weight | 200.0 mg. |

The active ingredient, lactose, maize starch and gelatinized maize starch are intimately mixed with one another. The mixture is passed through a comminuting machine and sebsequently moistened with water to a thick paste. The moiste mass is passed through a sieve, and the moist granulate is dried at 45° C. The dried granulate is thoroughly mixed with calcium stearate, and then the granulate is pressed to tablets weighing 200 mg. and having a diameter of about 8 mm.

EXAMPLE D

| Tablets | Per Tablet |
|---|---|
| (+)-(S)-1-{2-[4-(8-fluoro-10,11-dihydro-2-methyl-dibenzo[b,f]thiepin-10-yl)-1-piperazinyl]-ethyl}-2-pyrrolidinone maleate | 25.00 g. |
| Lactose | 110 g. |
| Maize Starch | 61.00 g. |
| Talc | 3.40 g. |
| Magnesium Stearate | 0.60 g. |
| | 200.00 g. |

The ingredients are intimately mixed with one another and pressed into tablets each weighing 200 mg. The tablets obtained are subsequently coated with ethylcellulose and Carbowax.

EXAMPLE E

| Capsules | Per Capsule |
| --- | --- |
| (+)-(S)-3-{2-[4-(8-fluoro-10,11-dihydro-2-methyl-dibenzo[b,f]thiepin-10-yl)-1-piperazinyl]ethyl}-2-oxazolidinone dimethanesulfonate | 29.0 mg. |
| Lactose | 156.0 mg. |
| Maize Starch | 30.0 mg. |
| Talc | 5.0 mg. |
| Total Weight | 220.0 mg. |

The active ingredient, lactose and maize starch are intimately mixed with one another and passed through a comminuting machine. The mixture is now thoroughly mixed with the talc and filled into hard gelatin capsules.

EXAMPLE F

| Capsules | Per Capsule |
| --- | --- |
| (+)-(S)-3-{2-[4-(8-fluoro-10,11-dihydro-2-methyl-dibenzo[b,f]thiepin-10-yl)-1-piperazinyl]-ethyl}-2-oxazolidinone | 25.5 mg. |
| Lactose | 159.5 mg. |
| Maize Starch | 30.0 mg. |
| Talc | 5.0 mg. |
| Total Weight | 220.0 mg. |

The active ingredient, lactose and maize starch are intimately mixed with one another and passed through a comminuting machine. The mixture is then thoroughly mixed with the talc and filled into hard shell gelatin capsules.

EXAMPLE G

| Parenteral dosage form | |
| --- | --- |
| Each 1 ml. ampul contains: | |
| (+)-(S)-3-{2-[4-(8-fluoro-10,11-dihydro-2-methyl-dibenzo[b,f]thiepin-10-yl)-1-piperazinyl]-ethyl}-2-oxazolidinone | 10.20 mg. (2% excess) |
| Methanesulfonic acid for injection | 2.17 mg. |
| Glucose for injection | 40.0 mg. |
| Water for injection q.s. ad | 1 ml. |

102 G. of active ingredient are dissolved in 2900 g. of ethanol and treated with 21.7 g. of methanesulfonic acid for injection. The ethanol is removed by distillation. The salt, dried to constant weight under strongly reduced pressure, is treated with 400 g. of glucose, dissolved in water for injection and made up to a volume of 10,000 ml. with water for injection. The solution is either filtered sterile and filled into colorless ampules which are gassed with nitrogen and sealed, or filled into colorless ampules, gassed with nitrogen, sealed and subsequently sterlized in a stream of steam for 30 minutes or autoclaved at 120° C.

I claim:

1. The (+)-(S)-enantiomer of 3-{2-[4-(8-fluoro-10,11-dihydro-2-methyl-dibenzo-[b,f]thiepin-10-yl)-1-piperazinyl]-ethyl}-2-oxazolidinone or a pharmaceutically acceptable acid addition salt thereof, essentially free of its (−)-(R)-enantiomer.

2. In accordance with claim 1, (+)-(S)-3-{2-[4-(8-fluoro-10,11-dihydro-2-methyl-dibenzo[b,f]thiepin-10-yl)-1-piperazinyl]-ethyl}-2-oxazolidinone, essentially free of its (−)-(R)-enantiomer.

* * * * *